United States Patent
Silvian

Patent Number: 5,700,280
Date of Patent: Dec. 23, 1997

[54] METHOD AND APPARATUS FOR CONTROLLING THE CHARGING PHASE OF AN IMPLANTABLE CARDIOVERTER-DEFRIBRILLATOR

[75] Inventor: Sergiu Silvian, La Crescenta, Calif.

[73] Assignee: Pacesetter, Inc., Sylmar, Calif.

[21] Appl. No.: 642,546

[22] Filed: May 3, 1996

[51] Int. Cl.$^6$ ............................... A61N 1/39
[52] U.S. Cl. ............................... 607/5
[58] Field of Search ............... 607/4, 5, 7, 8, 607/9, 11, 29

[56] References Cited

U.S. PATENT DOCUMENTS

| | | | |
|---|---|---|---|
| 5,193,538 | 3/1993 | Ekwell | 607/29 |
| 5,285,779 | 2/1994 | Cameron et al. | 607/5 |
| 5,318,591 | 6/1994 | Causey, III et al. | 607/5 |
| 5,447,522 | 9/1995 | Chang et al. | 607/7 |
| 5,470,341 | 11/1995 | Kuehn et al. | 604/5 |
| 5,488,553 | 1/1996 | Renger | 607/7 |

*Primary Examiner*—William E. Kamm
*Assistant Examiner*—George R. Evanisko

[57] ABSTRACT

The on time of a flyback converter is controlled without the need for a current-sensing resistor. Under one approach, an internal battery resistance $R_B$ is used as a substitute for the current-sensing resistor. The battery voltage $V_B$ decreases as a function of current drain from the battery due to the internal impedance. Charging control circuitry causes the on time to be terminated when the battery voltage $V_B$ falls below a predetermined reference voltage $V_R$, where $V_R = V_{B1} - \Delta \Delta V_B$. $V_{B1}$ represents the battery voltage before charging is commenced, and $\Delta V_B$ represents the drop in battery voltage from $V_{B1}$ when the battery current drain exceeds a predetermined maximum current. Under another approach, the charging control circuitry regulates the time out period $t_{on1} = K/V_B$, where K is a predetermined constant, such that it is 10–15 percent longer than the on time $t_{on}$.

13 Claims, 4 Drawing Sheets

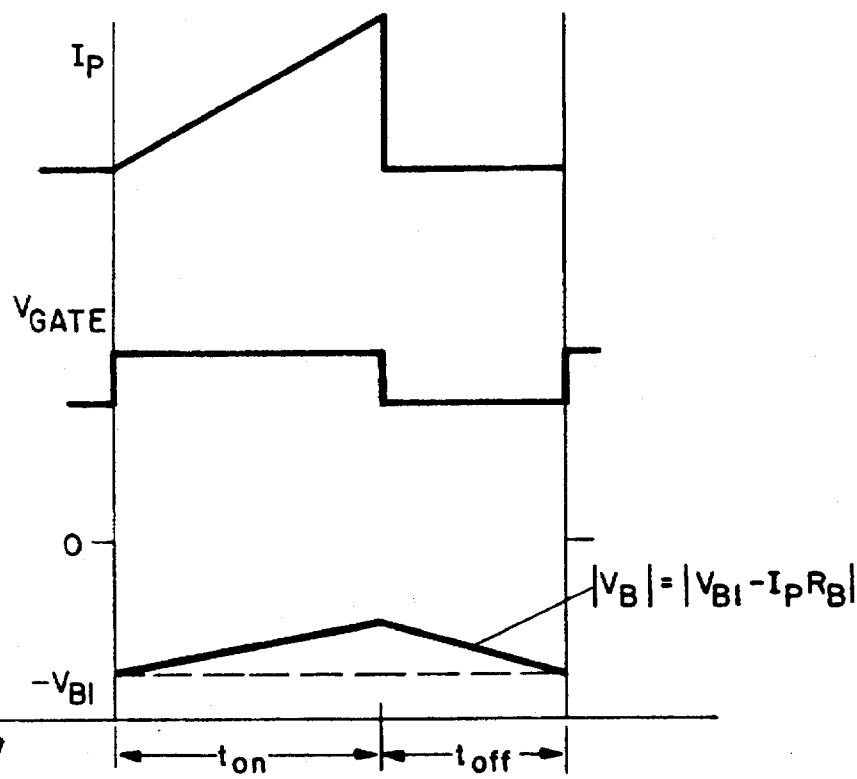
FIG. 2
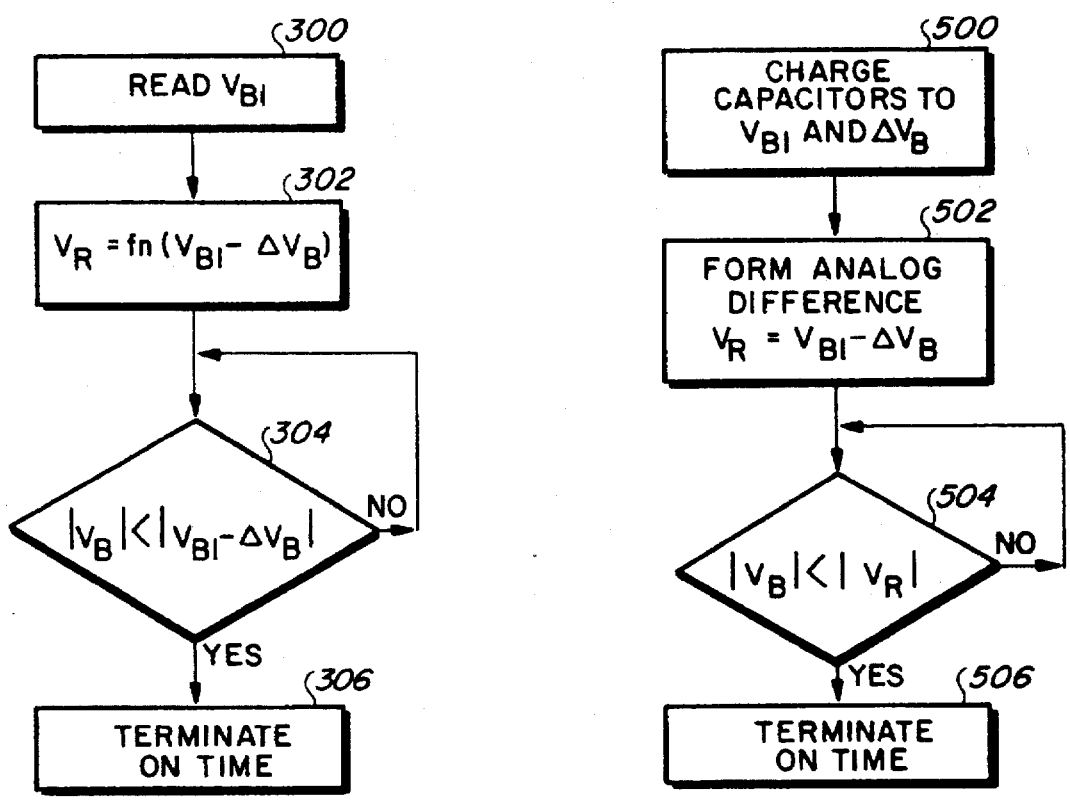
FIG. 3
FIG. 5

METHOD AND APPARATUS FOR CONTROLLING THE CHARGING PHASE OF AN IMPLANTABLE CARDIOVERTER-DEFRIBRILLATOR

BACKGROUND OF THE INVENTION

1. Field of the Invention

The present invention relates to implantable medical devices, and more particularly to methods and apparatus for regulating the charging phase of an implantable cardioverter-defibrillator (ICD).

2. Description of the Related Art

Implantable cardioverter-defibrillators generate high voltage shocks that are discharged from one or more shocking capacitors into a patient to perform either defibrillation or synchronized cardioversion. Typically, the electrical energy to power an ICD is supplied by a low voltage, long-lived power source, such as a lithium silver vanadium oxide battery. While the energy density of such power sources is relatively high, they do not have the high voltage and do not deliver the high current necessary to cardiovert or defibrillate the heart. Therefore, it is necessary to employ a DC-DC converter to convert electrical energy from a low voltage power supply to a high voltage level to be stored in a high energy storage capacitor. In general, as an example, a DC/DC converter will charge the capacitor in 5–10 seconds, and the capacitor will discharge in 2–5 milliseconds.

A popular type of DC-DC converter is the flyback converter, which employs a transformer having a primary winding in series with a primary power supply (typically a battery), and a secondary winding in series with high energy shocking capacitor(s). The conversion phase in which the capacitors are charged to a peak voltage is comprised of a series of charging cycles. During each cycle, the primary winding is coupled to and decoupled from the power supply by an interrupting switch. During the initial portion of the charging cycle, magnetic energy is stored in the transformer core. The current in the primary winding is then interrupted, and a collapsing field causes a current to develop in the secondary winding, which charges the high energy capacitors. By repeatedly coupling and decoupling the primary winding from the battery, the interrupting switch causes the shocking capacitors to be charged to a desired voltage in a relatively short period of time. When the capacitor voltage reaches the desired level, the charging phase is terminated and an output switch is closed to couple the capacitors to the cardiac tissue through shocking electrodes.

A patent to Causey et al., U.S. Pat. No. 5,318,591, discloses an ICD having a rapid high voltage charging circuit that uses the flyback method. The '591 patent discloses a charging circuit in which a primary winding of a transformer T1 is connected between a battery voltage at one end and a switch, realized with a transistor Q1, in series with a current-sensing resistor R1 on the other end. The switch Q1 is switched on and off under the control of an oscillator circuit 160.

The on time of the oscillator is limited so that the primary current does not exceed a maximum value. Above this maximum value, the ferrite core of the transformer will become saturated, which leads to energy losses. Conventional ICDs employ a current-sensing resistor to ensure that the primary current does not exceed the maximum value during charging. Such a resistor typically has a small value, on the order of 10–50 milliohms. At this low resistance, the resistance of the connection of the resistor component to the circuit board will cause an error in the measurement of the voltage drop across the resistor. Accordingly, to measure the voltage drop, a four-terminal Kelvin connection is typically used. The Kelvin connection is relatively bulky and occupies valuable space on the circuit board. Further, the maximum allowable primary current is typically on the order of eight amps. This current, when running through the current-sensing resistor, dissipates power on the order of 640 to 3,200 milliwatts. Therefore, one can see that it would be desirable to eliminate the current-sensing resistor in determining the on time of the flyback oscillator.

SUMMARY OF THE INVENTION

The present invention overcomes the disadvantages of the prior art by controlling the on time of a flyback converter without the need for a current-sensing resistor. In one embodiment of the invention, an inherent battery impedance $R_B$ is used as a substitute for the current-sensing resistor. A flyback transformer charges at least one shocking capacitor during a conversion phase, which is comprised of a number of charging cycles. A primary switching circuit couples a primary coil of the flyback transformer to the battery during an on time of the charging cycle and uncouples the primary coil from the battery during an off time of the charging cycle. The battery voltage $V_B$ decreases as a function of current drain from the battery due to the internal resistance.

Charging control circuitry of the present invention includes a comparator circuit for outputting a first reset signal when the battery voltage $V_B$ falls below a predetermined reference voltage $V_R$, where $V_R = V_{B1} - \Delta V_B$. $V_{B1}$ represents the battery voltage before starting the conversion phase, and $\Delta V_B$ represents the drop in battery voltage from $V_{B1}$ when the battery current drain exceeds a predetermined maximum current. According to the invention, the primary switching circuit includes a reset input for receiving the first reset signal. The primary switching circuit terminates the on time in response to the received first reset signal.

In one embodiment, a voltage measuring circuit measures $V_{B1}$ before the conversion phase. Processing logic, typically resident in a microprocessor, computes $V_R = V_{B1} - \Delta V_B$ and provides the reference voltage $V_R$ to the comparator circuit.

In another embodiment, the charging control circuitry includes a first sample-and-hold circuit and a second sample-and-hold circuit. Secondary switching circuitry couples the first sample-and-hold circuit to the battery before the conversion phase so as to hold $V_{B1}$, and couples the second sample-and-hold circuit to $\Delta V_B$ before the converter period so as to hold $\Delta V_B$. The secondary switching circuitry couples the first sample-and-hold circuit to the second sample-and-hold circuit in series during the conversion phase so as to provide a representation of the reference voltage $V_R$. The comparator circuit receives the representation of the reference voltage from the secondary switching circuitry.

In a further embodiment, the charging control circuitry includes a voltage measuring circuit for measuring $V_{B1}$ before the conversion phase. Timing control circuitry outputs a second reset signal to the reset input of the primary switching circuit such that time out period $t_{on1} = K/V_B$, where K is a predetermined constant that is 10–15 percent longer than the on time $t_{on}$.

BRIEF DESCRIPTION OF THE DRAWINGS

The objects, features and advantages of the present invention will be apparent to one skilled in the art in light of the following detailed description in which:

FIG. 2 illustrates a relationship between battery voltage and primary current.

FIG. 3 is a flowchart diagraming the flyback conversion process implemented by the flyback converter of FIG. 1.

FIG. 5 is a flowchart diagraming the process implemented by the flyback converter of FIG. 4.

DETAILED DESCRIPTION OF THE INVENTION

The present invention provides a method and apparatus for controlling the charging phase of an ICD. For purposes of explanation, specific details are set forth to provide a thorough understanding of the present invention. However, it will be understood by those skilled in the art, from reading this disclosure, that the invention may be practiced without these details. Moreover, well-known elements, devices, process steps and the like are not set forth in order to avoid obscuring the invention.

The present invention controls the on time of a flyback converter, while eliminating the need for a current-sensing resistor to terminate the on time when the primary current has reached a predetermined maximum. According to one approach of the present invention, the battery impedance $R_B$ is used as a substitute for the current-sensing resistor.

Figure 1:
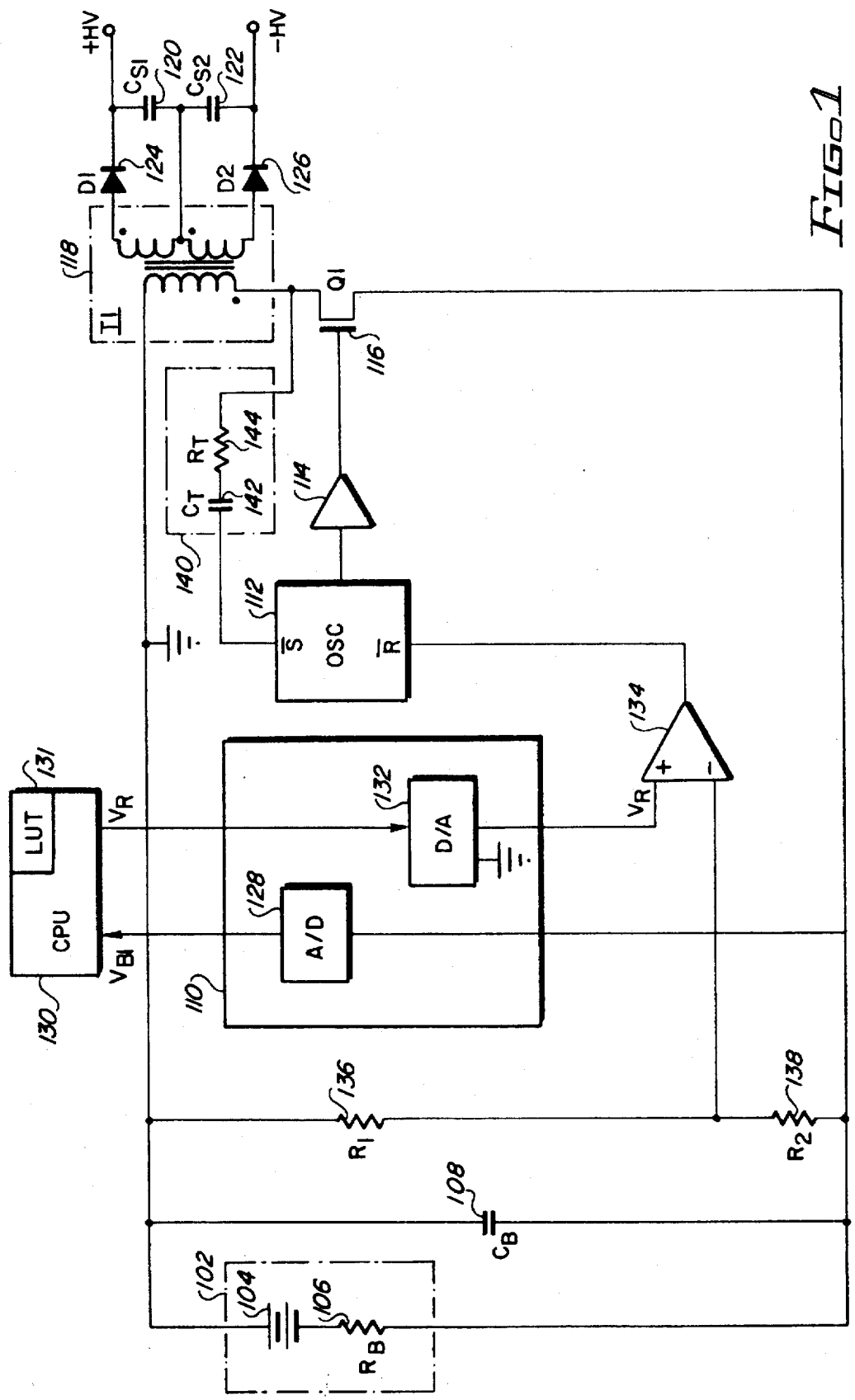
FIG. 1 illustrates an embodiment of the flyback converter of the present invention.

Referring to FIG. 1, a battery 102 may be represented as an ideal battery 104 in series with an internal battery resistance $R_B$ 106. The battery 102 is coupled in parallel to a bypass capacitor $C_B$ 108.

The flyback converter also includes a control circuit 110 and a switching circuit that preferably includes a free-running oscillator 112, a driver 114, and a power FET switch Q1 116. The oscillator preferably generates a square wave, which is passed through the driver 114 and applied to the gate of the power FET Q1 116. Under control of the oscillator 112, the power FET 116 couples or uncouples a primary coil of a transformer T1 118 from the battery 102. The secondary coil of the transformer 118 is coupled to two charging capacitors $C_{S1}$ 120 and $C_{S2}$ 122 through diodes D1 124 and D2 126 in order to charge the shocking capacitors $C_{S1}$ 120 and $C_{S2}$ 122 to the shocking voltage.

The control circuit 110 includes an A/D converter 128 that provides a digital measurement of the voltage $V_B$ of the battery 102 to a microprocessor or other processing logic 130 in the ICD. It should be noted that in the described embodiment, $+V_B$ is ground and all the voltages are measured referred to that ground. The microprocessor 130 returns a negative reference voltage $V_R$ through a digital-to-analog converter 132 (D/A) in the control circuit 110. The analog form of the reference voltage $V_R$ is coupled to a non-inverting input of a comparator 134. The flyback converter preferably includes a voltage divider comprising a first resistor R1 136 and a second resistor R2 138. The voltage divider is tapped so as to provide the voltage across R1 136 to an inverting input of the comparator 134. The battery voltage is typically on the order of 2–3 V. However, because the common mode range of the comparator is from ground to approx. $-2$ V and the magnitude of the output of the D/A 132 ($V_R$) is less than the magnitude of the battery voltage ($V_B$), it is preferable to use the voltage divider to provide the voltage across R1 136 to the inverting input of the comparator 134 as a representation of the battery voltage $V_B$.

The output of the comparator 134 is fed into a reset input of the oscillator 112. A set input of the oscillator 112 is coupled to a flyback termination detection circuit 140. The flyback termination detection circuit 140 comprises a capacitor $C_T$ 142 and a resistor $R_T$ 144.

The flyback converter takes advantage of the internal battery resistance to eliminate the need for a current-sensing resistor to detect the maximum primary charging current. FIG. 2 illustrates the relationship between the battery voltage and the primary current. During the oscillator on time $t_{on}$, the oscillator 112 (FIG. 1) drives a voltage into the gate of the FET 116 (FIG. 1) to close the FET switch and charge the primary winding of the transformer T1 118 (FIG. 1). The primary current $I_p$ increases linearly according to the relationship:

$$\Delta I_p = \frac{V_p}{L_p} \Delta t \tag{1}$$

where $L_p$ is the inductance of the primary and $V_p$ is the voltage across the primary. Assuming for now that $C_B$ 108 (FIG. 1) is not connected, the voltage across the battery 102 (FIG. 1) is determined by the equation $$|V_B|=|V_{B1}|-\Delta V_B \tag{2}$$

where $V_{B1}$ is the battery voltage before the converter is started, and $\Delta V_B = I_p * R_B$. Further, it is known that the battery resistance $R_B$ 106 (FIG. 1) remains fairly constant over the life of the battery.

According to the equation, as the primary current increases, the voltage drop across the battery resistance $R_B$ 106 (FIG. 1) increases, which has the effect of decreasing the voltage $V_B$ of the battery 102 (FIG. 1). In practice, some of this voltage drop is compensated by energy returned from the bypass capacitor $C_B$ 108 (FIG. 1) to smooth out the ripple in the battery voltage. In a more complete sense, the battery voltage drop is a function not only of the primary current and the battery resistance, but also the bypass capacitor 108 (FIG. 1) and other loads, such as the control circuit 110 (FIG. 1). In any event, it can be seen that there exists a relationship between the primary current and the battery voltage.

Because of the effects of the bypass capacitor 108 (FIG. 1) and other loads on the battery 102 (FIG. 1), the relationship between the battery voltage $V_B$ and the primary current $I_p$ is preferably established experimentally during the design of the flyback converter of the present invention. The relationship between selected values of the maximum allowable primary current and the drop in battery voltage $\Delta V_B$ is preferably stored in a lookup table 131 (FIG. 1) in the microprocessor 130 (FIG. 1).

With reference to FIG. 1 and the flow chart of FIG. 3, the flyback converter operates as follows. Before initiating the conversion phase, the microprocessor reads the absolute value of the battery voltage $V_{B1}$ (loaded down by the bypass capacitor and other loads) from the A/D 128 (step 300). For a selected maximum primary current $I_{max}$, the microprocessor 130 computes a reference voltage $V_R$ as follows:

$$V_R = \frac{R1}{R1+R2} * (V_{B1} - \Delta V_B) \tag{3}$$

where $\Delta V_B$ is the battery voltage drop corresponding to $I_{max}$. The value $\Delta V_B$ is obtained from the microprocessor lookup table 131 (step 302).

This reference voltage $V_R$ is input to the D/A 132, which passes the analog signal $V_R$ to the comparator 134. When the primary current $I_p$ reaches the maximum $I_{max}$, the battery voltage $V_B$ decreases by $\Delta V_B$. This in turn causes the absolute value of the voltage across the resistor R1 136 to fall below $V_R$ (step 304) (i.e., $|V_B|<|V_{B1}-\Delta V_B|$). When this occurs, the output of the comparator 134 falls low. This action resets the oscillator 112 to terminate its on time, thereby terminating the charging of the primary (step 306).

Note that because $V_R$ depends upon a ratio of resistances, the resistors R1 136 and R2 138 need not have small resistances like the current-sensing resistor of the prior art, and thus do not require bulky Kelvin connections.

During the time the oscillator is off, flyback occurs. A linearly decreasing flyback current flows through the secondary, and causes a positive voltage to appear at the drain of the power FET Q1 116. When the flyback current reduces to zero, the drain voltage will sharply fall to zero. Many conventional flyback converters use a fixed off time for the oscillator 112. However, it is desirable to terminate the off time early and start the charging of the primary when the flyback cycle has ended. Any additional time that the oscillator is on will result in an energy loss due to the self-oscillation of the transformer windings.

The capacitor $C_T$ 142 in the flyback termination detector 140 AC couples the drain voltage to the active-low set input of the oscillator 112 so as to sense the falling edge of the drain voltage when the flyback current falls to zero. This provides a very quick method for truncating the off time of the oscillator, and for restarting the charging of the primary.

Typically, the drain voltage is on the order of twenty volts. However, because the converter is preferably implemented in CMOS, voltages applied to CMOS components must be limited to approximately three volts. Therefore, the resistor $R_T$ 144 is selected to limit the voltage applied to the oscillator 112 appropriately.

Figure 4:
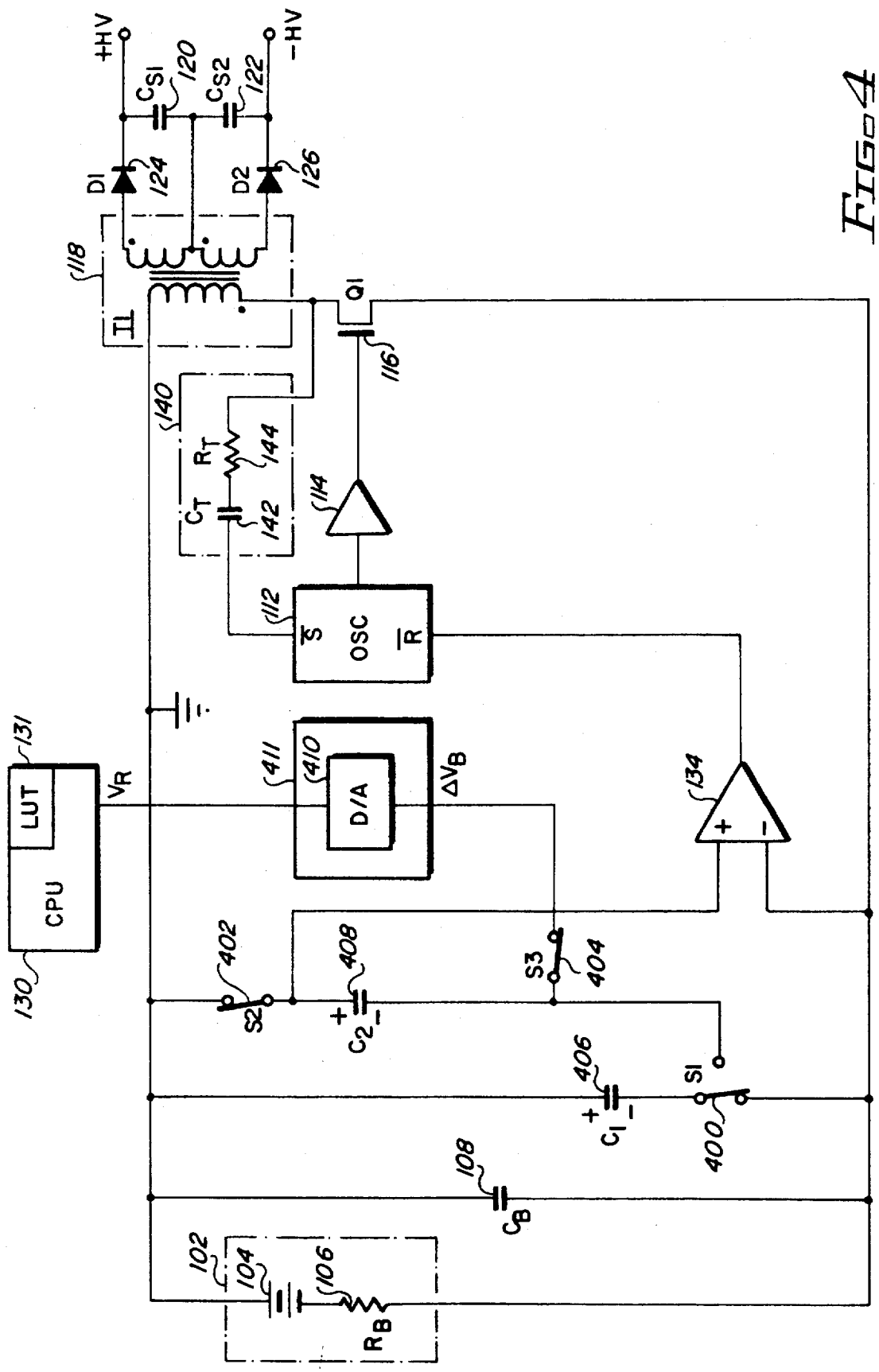
FIG. 4 illustrates an alternative embodiment of the flyback converter of the present invention.

FIG. 4 illustrates another embodiment of the flyback converter of the present invention that regulates the oscillator on time according to the change in battery voltage. FIG. 5 is a flowchart illustrating the process steps of this embodiment. Unlike the embodiment of FIG. 1, this circuit eliminates the need for the microprocessor to measure the battery voltage before charging is initiated.

As can be seen from FIG. 4, this flyback converter circuit includes many of the same elements as that of FIG. 3. However, this embodiment employs sample-and-hold circuits to store the pre-charge battery voltage and $\Delta V_B$. As shown in FIG. 4, switches S1 400, S2 402 and S3 404 are positioned before the conversion phase is initiated so that a sample-and-hold capacitor $C_1$ 406 is charged to the battery voltage and a sample-and-hold capacitor $C_2$ 408 is charged to the value $\Delta V_B$ (step 500). The analog value $\Delta V_B$ is provided by a D/A 410, which receives the digital value $\Delta V_B$ from the microprocessor 130.

A control circuit 411, which includes the D/A 410, then initiates charging, whereby the FET switch Q1 116 is closed to start the converter. During this on time, the switches S1 400, S2 402 and S3 404 are reconfigured so that the switches S2 402 and S3 404 are opened. Further, the switch S1 400 is switched so that the capacitors C1 406 and C2 408 are placed in series. As a result, the value $-(V_{B1}-\Delta V_B)=-V_R$ is presented to the non-inverting input of the comparator 134 (step 502). The voltage $-V_B$ is presented to the inverting input of the comparator 134. Thus, when the magnitude of the battery voltage $V_B$ falls below the magnitude of the voltage $V_R$, the comparator output goes low (step 504), thereby terminating the on time of the oscillator 112 through its active low reset input (step 506).

Those skilled in the art will understand that the sample-and-hold circuit formed by the switch S1 400 and the capacitor C1 406 may, without loss of generality, incorporate a voltage divider to operate on a fraction of the battery voltage, rather than on the full battery voltage, and receive a similarly scaled $\Delta V_B$ from the microprocessor.

It can be appreciated that by holding the precharged battery voltage value $V_{B1}$ in the capacitor $C_1$ 406, the flyback converter of FIG. 4 avoids the need for the microprocessor to measure that voltage.

The flyback converters that have been discussed terminate the flyback oscillator on time $t_{on}$ when the primary current $I_p$ reaches a maximum value $I_{max}$. As a measure of protection if this mechanism fails, the oscillator has a timeout period $t_{on1}$ that is 10–15 percent longer than $t_{on}$. However, the battery voltage decreases as the battery approaches its end of life. Accordingly, the on time ton will increase over time to reach the maximum-set primary current (see equation 1 above). Consequently, $t_{on1}$ (if constant) shall be larger than the $t_{on}$ at minimum $V_B$. At maximum $V_B$, if peak current measurement (as described) fails, the corresponding peak current can reach dangerously high levels. Taking this into account, the flyback converters of the present invention preferably include circuitry for regulating the time-out $t_{on1}$ of the oscillator 112.

Figure 6:
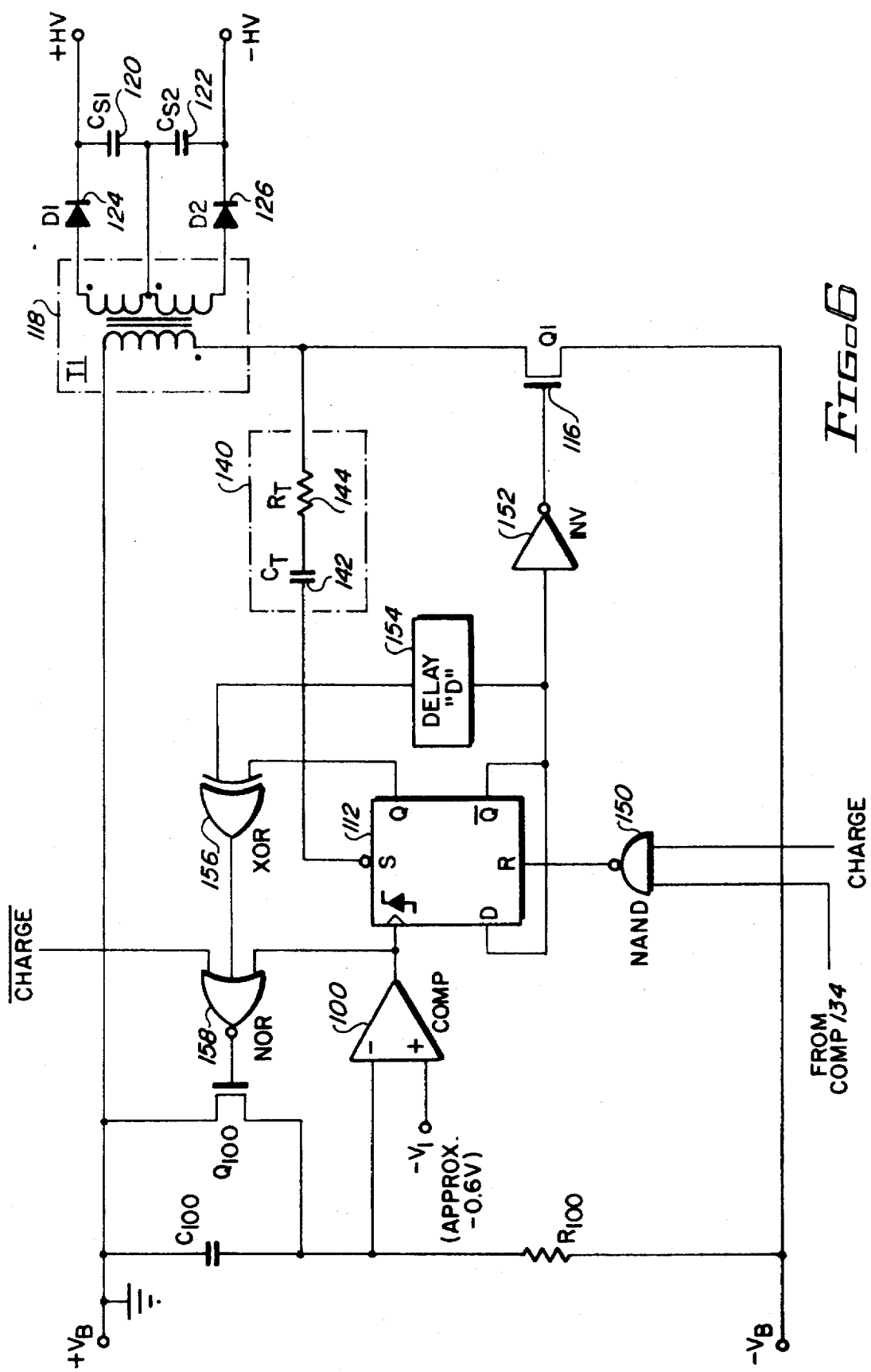
FIG. 6 illustrates the oscillator of FIG. 1 implementing $t_{on1}=K/V_B$.

FIG. 6 depicts circuitry that may be used in connection with the oscillator 112 to make the oscillator time out period $t_{on1}$ 10–15% longer than the oscillator on time ton irrespective of the battery voltage. The circuit components used to implement this feature include a resistor 146, a comparator 148, a capacitor 150, a NOR gate 152, a delay buffer 154, a NAND gate 156, an exclusive OR (XOR) gate 158, a FET switch Q 162 and an invertor 160. In this embodiment, the invertor 160 provides an input signal to the FET Q1 116 instead of the driver 114 (FIGS. 1 and 4). The output of the comparator 134 (FIGS. 1 and 4) is provided as input to the NAND gate 156 along with a high signal input CHARGE from the CPU 130 (FIGS. 1 and 4) through an invertor. The output of the NAND gate 156 is supplied to the active high reset of the oscillator 112. The resistor 146 and the capacitor 150 are coupled in series across the battery 102 (FIGS. 1 and 4). The RC time constant of the resistor 146 and the capacitor 150 is used to produce a negative-going saw-tooth wave with a frequency that is twice the driving frequency of the FET Q1 116. The saw-tooth wave is received at the inverting input of the comparator 148.

The noninverting input of the comparator 148 is coupled to a reference voltage supply $-V1$ of approximately $-0.6$ volts. The output of the comparator 148 is coupled to the clock input of the oscillator 112. When the capacitor 150 is discharged (i.e., the low point of the saw-tooth wave), the output of the comparator 148 goes high. This provides a leading edge to the clock input of the oscillator 112 causing it to reverse the state of its Q and Q-bar outputs. The output of the comparator 148 is also provided as an input to the NOR gate 152. The NOR gate 152 also receives a low signal input CHARGE-bar from the CPU along with the output of the XOR gate 158 as inputs. When the output of the NOR gate 152 is low the FET Q1 162 opens causing the capacitor 150 to discharge.

The XOR gate 158 receives inputs from the Q and Q-bar outputs of the oscillator 112. The Q-bar output is delayed by the delay buffer 154 before being supplied to the XOR gate 158. The delay buffer 154 generates a short negative-going pulse everytime the oscillator 112 changes states. The Q-bar output is also supplied to the inverter 160. The invertor 160 provides the drive necessary to drive the power FET Q1 116. The output of the invertor 160 opens and closes the FET switch Q1 116.

The time out period $t_{on1}$ is determined by the capacitor 150, the resistor 146 and the reference voltage $-V1$. As the battery voltage increases so does the speed of charging of the capacitor 150, such that $t_{on1}=K/V_B=t_{on}$. This relation is similar to the transformer primary current from equation (1):

$$t_{on} = \frac{Ipeak \cdot L_p}{V_B} \quad (4)$$

In this way, $t_{on1}$ can always be 10–15 percent longer than $t_{on}$ without regard to the battery voltage. It should be noted that $t_{on1}$ as adjusted will always be overridden by the flyback termination detector 140, such that the capacitor $C_T$ 142 couples the drain voltage to the active-low set input of the oscillator 112 so as to sense the falling edge of the drain voltage when the flyback current falls to zero. Thus by using the circuit of FIG. 6, even if the peak primary current measurement fails, no dangerous currents are generated.

It will be appreciated that various modifications and alterations might be made by those skilled in the art without departing from the spirit and scope of the present invention. The invention should, therefore, be measured in terms of the claims which follow.

What is claimed is:

1. An implantable cardioverter-defibrillator having a shocking capacitor chargeable during a conversion phase, comprising:

a battery having an internal battery resistance and a battery voltage that decreases as a function of current drain from the battery due to the internal battery resistance;

flyback transformer means for charging the shocking capacitor during the conversion phase, said conversion phase comprising a series of charging cycles, the flyback transformer means including a primary coil;

charging control means including comparator means for outputting a first reset signal when the battery voltage $V_B$ falls below a predetermined reference voltage $V_R$, wherein $V_R=V_{B1}-\Delta V_B$, where $V_{B1}$ represents the battery voltage before the conversion phase, and $\Delta V_B$ represents a maximum drop in battery voltage from $V_{B1}$ when the battery current drain exceeds a predetermined maximum current, the charging control means comprising:

voltage measuring means for measuring $V_{B1}$ before the conversion phase; and processing logic means for computing $V_R=V_{B1}-\Delta V_B$ and for providing $V_R$ to the comparator means;

primary switching means for coupling the primary coil of the flyback transformer to the battery during an on time of a charging cycle and uncoupling the primary coil from the battery during an off time of a charging cycle; and wherein the primary switching means includes a reset input for receiving the first reset signal, wherein the primary switching means terminates the on time in response to the received first reset signal.

2. The implantable cardioverter-defibrillator of claim 1, wherein the charging control means comprises:

first sample-and-hold means;

second sample-and-hold means; and secondary switching means for coupling the first sample-and-hold means to the battery before the conversion phase so as to hold $V_{B1}$, for coupling the second sample-and-hold means to $\Delta V_B$ before the conversion phase so as to hold $\Delta V_B$, and for coupling the first sample-and-hold means to the second sample-and-hold means in series during the conversion phase so as to provide a representation of the reference voltage $V_R=V_{B1}-\Delta V_B$, wherein the comparator means receives the representation of the reference voltage from the secondary switching means.

3. The implantable cardioverter-defibrillator of claim 2, wherein the charging control means further comprises processing logic means for providing $\Delta V_B$ to the secondary switching means.

4. The implantable cardioverter-defibrillator of claim 1, wherein the charging control means further comprises:

voltage measuring means for measuring the battery voltage $V_{B1}$ before the conversion phase; and timing control means for outputting a second reset signal to the reset input of the primary switching means to limit the on time to a time $t_{on}=K/V_{B1}$, where K is a predetermined constant.

5. The implantable cardioverter-defibrillator of claim 1, wherein the primary switching means comprises an oscillator.

6. An implantable cardioverter-defibrillator having a shocking capacitor chargeable during a conversion phase, comprising:

a battery having an internal battery resistance and a battery voltage that decreases as a function of current drain from the battery due to the internal battery resistance;

flyback transformer means for charging the shocking capacitor during the conversion phase, said conversion phase comprising a series of charging cycles, the flyback transformer means including a primary coil;

primary switching means for coupling the primary coil of the flyback transformer to the battery during an on time of a charging cycle and uncoupling the primary coil from the battery during an off time of a charging cycle;

a reset input, coupled to the primary switching means, for receiving a first reset signal, wherein the primary switching means terminates the on time in response to the received first reset signal; and charging control means including voltage measuring means for measuring the battery voltage $V_{B1}$ before the conversion phase, and timing control means for outputting the first reset signal to the reset input of the primary switching means to limit the on time to a time $t_{on}=K/V_{B1}$, where K is a predetermined constant, said charging control means further comprising comparator means for outputting a second reset signal to the reset input of the primary switching means when the battery voltage $V_B$ falls below a predetermined reference voltage $V_R$, wherein $V_R=V_{B1}-\Delta V_B$, where $V_{B1}$ represents the battery voltage before the conversion phase, and $\Delta V_B$ represents the drop in battery voltage from $V_{B1}$ when the battery current drain exceeds a predetermined maximum current;

voltage measuring means for measuring $V_{B1}$ before the conversion phase; and processing logic means for computing $V_R=V_{B1}-\Delta V_B$ and for providing $V_R$ to the comparator means; and wherein the primary switching means terminates the on time in response to the received second reset signal and wherein the primary switching means terminates the on time in response to the received second reset signal.

7. The implantable cardioverter-defibrillator of claim 6, wherein the charging control means comprises:

first sample-and-hold means;

second sample-and-hold means; and secondary switching means for coupling the first sample-and-hold means to the battery before the conversion phase so as to hold $V_{B1}$, for coupling the second sample-and-hold means to $\Delta V_B$ before the conversion phase so as to hold $\Delta V_B$, and for coupling the first sample-and-hold means to the second sample-and-hold means in series during the conversion phase so as to provide a representation of the reference voltage $V_R = V_{B1} - \Delta V_B$, wherein the comparator means receives the representation of the reference voltage from the secondary switching means.

8. The implantable cardioverter-defibrillator of claim 7, wherein the charging control means further comprises processing logic means for providing $\Delta V_B$ to the secondary switching means.

9. The implantable cardioverter-defibrillator of claim 6, wherein the primary switching means comprises an oscillator.

10. A method of operating an implantable cardioverter-defibrillator including a shocking capacitor and a battery having an internal battery resistance and a battery voltage that decreases as a function of current drain from the battery due to the internal battery resistance, the method comprising the steps of:

using a flyback transformer to charge the shocking capacitor during a conversion phase, said conversion phase a series of charging cycles, the flyback transformer including a primary coil;

generating a first reset signal when the battery voltage $V_B$ falls below a predetermined reference voltage $V_R$, wherein $V_R = V_{B1} - \Delta V_B$, $V_{B1}$ representing the battery voltage before the conversion phase, and $\Delta V_B$ representing a maximum drop in battery voltage from $V_{B1}$ when the battery current drain exceeds a predetermined maximum current;

coupling the primary coil of the flyback transformer to the battery during an on time of a charging cycle and uncoupling the primary coil from the battery during an off time of a charging cycle;

coupling a first sample-and-hold circuit to the battery before the conversion phase so as to hold $V_{B1}$;

coupling a second sample-and-hold circuit to $\Delta V_B$ before the conversion phase so as to hold $\Delta V_B$; and coupling the first sample-and-hold circuit to the second sample-and-hold circuit in series during the conversion phase so as to provide a representation of the reference voltage $V_R = V_{B1} - \Delta V_B$; and terminating the on time of a charging cycle in response to the first reset signal.

11. The method of claim 10 further comprising the steps of:

measuring the battery voltage $V_{B1}$ before the conversion phase; and providing a second reset signal to limit the on time to a time $t_{on} = K/V_{B1}$, where K is a predetermined constant.

12. A method of operating an implantable cardioverter-defibrillator including a shocking capacitor and a battery having an internal battery resistance and a battery voltage that decreases as a function of current drain from the battery due to the internal battery resistance, the method comprising the steps of:

using a flyback transformer to charge the shocking capacitor during a conversion phase, said conversion phase comprising a series of charging cycles, the flyback transformer including a primary coil;

coupling the primary coil of the flyback transformer to the battery during an on time of a charging cycle and uncoupling the primary coil from the battery during an off time of a charging cycle;

terminating the on time in response to a first reset signal;

measuring the battery voltage $V_{B1}$ before the conversion phase;

generating the first reset signal to limit the on time to a time $t_{on} = K/V_{B1}$, where K is a predetermined constant;

generating a second reset signal when the battery voltage $V_B$ falls below a predetermined reference voltage $V_R$, wherein $V_R = V_{B1} - \Delta V_B$, wherein $V_{B1}$ represents the battery voltage before the conversion phase, and $\Delta V_B$ represents the drop in battery voltage from $V_{B1}$ when the battery current drain exceeds a predetermined maximum current, and terminates the on time in response to the second reset signal; and using a second sample-and-hold means before the conversion phase so as to sample-and-hold $\Delta V_B$, using a first sample-and-hold means in series with the second sample-and-hold means during the conversion phase so as to provide a representation of the reference voltage $V_R = V_{B1} - \Delta V_B$, wherein the comparator means receives the representation of the reference voltage from the secondary switching means.

13. The method of claim 12 further comprising the steps of:

coupling a first sample-and-hold circuit to the battery before the conversion phase so as to hold $V_{B1}$;

coupling a second sample-and-hold circuit to $\Delta V_B$ before the conversion phase so as to hold $\Delta V_B$; and coupling the first sample-and-hold circuit to the second sample-and-hold circuit in series during the conversion phase so as to provide a representation of the reference voltage $V_R = V_{B1} - \Delta V_B$.

* * * * *